United States Patent [19]

Sternberger

[11] 4,392,996

[45] Jul. 12, 1983

[54] PROCESS FOR THE PREPARATION OF BIOLOGICALLY ACTIVE PEPTIDE ANALOGUES

[75] Inventor: Ludwig A. Sternberger, Rochester, N.Y.

[73] Assignee: The University of Rochester, Rochester, N.Y.

[21] Appl. No.: 282,910

[22] Filed: Jul. 13, 1981

[51] Int. Cl.$^3$ ............................................. C07G 7/00
[52] U.S. Cl. ...................... 260/112 R; 260/112.5 LH; 424/95; 424/108; 424/109
[58] Field of Search .................... 260/112 R, 112.5 R, 260/112.5 LH; 424/95, 108, 109, 177

[56] References Cited

PUBLICATIONS

Scharrer, E., Res. Publ. Assn. Nervous and Mental Disease, 20:170, 1939.
Scharrer, B., Gen. Comp. Endocrin, 34:50, 1978.
Bargmann, W., Z. Zellforsch, 34:610, 1949.
Matsao, H., Biochem. Biophys. Res. Commun., 43:1334, 1971.
Chang, M. M., J. Biol. Chem., 245:4784, 1970.
Cox, B. M., Proc. Natl. Acad. Sci., 73:1821, 1976.
Mains, R. E., Proc. Natl. Acad. Sci., USA, 74:3014, 1977.
Sternberger, L. A., J. Histochem. Cytochem., 27:1424, 1979.
Arimura, A., Endocrinology, 91:529, 1972.
Sternberger, L. A., J. Histochem. Cytochem., 18:315, 1970.
Sternberger, L. A., Cell. Tiss. Res., 162:141, 1975.
Sternberger, L. A., Endocrinology, 102:63, 1978.
Cuatrecasas, P., Advanced Nucleotide Res., 5:79, 1975.
Labrie, F., The Endocrine Functions of The Brain, Raven Press, N. Y., 1980.
Watkins, W. B., Neurosci. Letts., 17:329, 1980.
Sternberger, L. A., Exp. Mol. Path., 4:112, 1965.
Lindstrom, J., Ann, NY Acad. Sci., 274:254, 1976.
Sternberger, L. A., Neuroendocrinology, 25:111, 1978.
Adams, J. C., Neuroscience, 2, 141–145, 1977.
Solik, H., Endocrinology, 105, 21–26, 1979.
Tougard, C., J. Histochem. Cytochem., 27, 1630–1633, 1979.
Sternberger, L. A., J. Histochemistry & Cytochemistry, vol. 25, pp. 1036–1042, 1977.
Sternberger, L. A., J. Histochemistry & Cytochemistry, vol. 27, pp. 1430–1437, 1979.
Sternberger, L. A., Immunochemistry, John Wiley & Sons, N. Y., pp. 104–169, 231–293, 1979.

*Primary Examiner*—John C. Bleutge
*Assistant Examiner*—Patricia Short
*Attorney, Agent, or Firm*—Martin Lukacher

[57] ABSTRACT

Previously unknown biologically active peptide analogues are isolated by mixing a known biologically active peptide with an affinity medium and separating the unknown peptide analogue by techniques such as liquid chromotography or electrophoresis. These biologically active peptide analogues react with receptors and thus act as hormones which have a more discriminating and longer lasting hormonal action than the original peptide.

5 Claims, No Drawings

PROCESS FOR THE PREPARATION OF BIOLOGICALLY ACTIVE PEPTIDE ANALOGUES

DESCRIPTION

1. Background of the Invention

This invention relates to the discovery, isolation and use of hitherto unsuspected biologically active peptide analogues, in particular, neuropeptides, that behave as analogues to neuropeptides known so far on the basis of isolation by conventional methods. The invention enlarges the scope of neuroendocrinology, provides normal and simple methods of isolation of hitherto unkown factors, and may yield many hormones whose actions are more selective than those previously known.

The universality of neurohormones, later known as neuropeptides, as a fundamental biologic system of both hormonal and neurotransmitter actions has been predicted by Ernst and Berta Scharrer as early as 1939 (see, Scharrer, E., Scharrer B., Res. Publ. Assn. Nervous and Mental D 20:170, 1939 and Scharrer B., Gen. Comp. Endocrin, 34:50, 1978). Subsequent isolation of minute quantities of highly active peptides from pools of thousands of brains has been followed by synthesis, experimental and clinical use of over 20 peptides, of which vasopressin (see, Bargmann W., Z. Zellforsch 34:610, 1949), luteinizing hormone-releasing hormone, hereinafter referred to througout this specification as LHRH, (see, Matsao H, Bab Y, Nair R M, Arimara A, Schally A., Biochem. Biophys. Res. Commun. 43:1334, 1971, and Burgus R, Amoss M, Brazeau P, Brown M, Ling N, Rivier C, Rivier J, Vale W, Villarreal J. in Labrie F, Meites J, Pelletier G (eds), Hypothalamus and Endocrine Functions, New York, Plenum Press, 1976), substance P (see, Chang M M, Leeman S E., J. Biol. Chem. 245:4784, 1970), neurotensin (see, Carraway R, Leeman S E. J. Biol. Chem., 248:6854, 1973), thyrotropin releasing hormone, beta endorphin (see, Cox B M, Goldstein A, Li C H., Proc. Natl. Acad. Sci., 73:1821, 1976), and gastrointestinal peptides (widely distributed in many organs, including brain) are just a few examples (see, Sternberger L. A., Immunocytochemistry, 2nd Edition, John Wiley and Sons, New York, 1979). Many of these substances have several actions. For instance, LHRH releases both luteinizing hormone, hereinafter referred to as LH, and follicle-stimulating hormone, hereinafter referred to as FSH, from the pituitary, while affecting sexual behavior by direct action in the brain. Vasopressin acts as antidiuretic hormone, improves memory, raises blood pressure and may affect secretion of ACTH. The peptides are not synthesized on ribosomes as such, but instead, a larger molecule (precursor) is formed. The precursors are enzymatically broken down to yield the peptides of known biologic action. At least in one system, the proopiomelanocortin system (see, Mains R E, Eipper B, Ling N., Proc. Natl. Acad. Sci. USA, 74:3014, 1977), the precursor mRNA has been isolated and its homologous DNA nucleotide sequence determined. Enzymatic cleavage of this precursor leads to at least six small fragments of biologic activity. They are beta lipotropin, beta endorphin, gamma endorphin, beta-MSH, alpha-MSH and ACTH. Recent data suggest (see, Sternberger L A, Joseph S A. J. Histochem. Cytochem., 27:1424, 1979, and Joseph SA, Sternberger L A., J. Histochem. Cytochem., 27:1430, 1979) that this pattern of assembly and breakdown is only a special case and that some of the same small peptides found in proopiomelanocortin may also occur in combination with different peptides in other, yet unknown precursors. With the use of monoclonal antibodies it can be shown that the diversity of neuropeptides expressed as antigens is highly specific, thus leading to the suspicion that most of existing neuropeptides have not yet been discovered.

LHRH releases FSH and LH indiscriminately (see, Arimura A, Debelynk L, Schally A V., Endocrinology, 91:529, 1972). Ovulation and menstruation are, however, processes that require fine tuned release of LH and FSH at proportions varying in different phases of the cycle. As long as the hormonal factors responsible for this fine tuning are unknown, the therapeutic value of LHRH remains limited. Similar limitations apply to other peptides isolated so far.

The immunocytochemical localization of peptides in brain and periphery is being widely studied by light and electron microscopy with the unlabeled antibody PAP method (see, Sternberger L A., Immunocytochemistry, 2nd Edition, John Wiley and Sons, New York, 1979, and Sternberger L A, Hardy P H, Jr., Cuculis J J, Meyer H G., J. Histochem. Cytochem., 18:315, 1970). One way of making the specificity of localization plausible is neutralization of the antibodies used for immunocytochemical detection of a given peptide by preincubation of the antibodies with this peptide. Immunocytochemistry does not only permit the localization of neuropeptides at production sites (endocrine cells, neurons and neuronal projections), but also at their receptor sites of action (see, Sternberger L A. Immunocytochemistry, 2nd Edition, John Wiley and Sons, New York, 1979; Sternberger L A, Petrali J P., Cell Tiss. Res., 162:141, 1972, and Sternberger L A, Petrali J P, Joseph S A, Meyer H G, Mills K R., Endocrinology, 102:63, 1978).

It is well known that receptors in target cells are the first encounter of a hormone and its action. Action on a receptor, properly established as reversibly binding the hormone with high affinity in a saturable manner, often cooperatively, and linked with a second messenger, is prima facie evidence of the activity of a hormone (see, Cuatrecasas P., Advanced Nucleotide Res., 5:79, 1975; DeKoning J, van Dieter JAMJ, van Ress G P., Mol. Cell. Endocrin., 5:151, 1976; Labrie F, Godbout M, Lagace L, Massicotte J, Furland L, Burdeu N, Boulieu J, Lepine J, Lissitsky J-C, Raymond V, Borgeut P, Beaulieu M, Veilleux R in Motta, M (ed), The Endocrine Functions of the Brain, Raven Press, New York, 1980; and Watkins W B., Neurosci, Letts. 17:329, 1980). This evidence is strengthened if the concentration of the hormone necessary for reaction with receptors is the same as that required for its physiologic effects (minimal concentration as well as concentration required for one-half saturation of receptor and one-half maximum physiologic effect). In the case of LHRH, parallelism of pituitary LHRH radioligand receptor binding and LH release is satisfied quantitatively (see, Labrie F, Godbout M, Lagace L, Massicotte J, Furland L, Burdeu N, Boulieu J, Lepin E J, Lissitsky J-C, Raymond V, Borgeut P, Beaulieu M, Veilleux R in Motta, M (ed), The Endocrine Functions of the Brain, Raven Press, New York, 1980). Studies have provided immunocytochemical binding constants (concentration that gives 50% binding) for LHRH receptors as $10^{-8}$ and $10^{-10}$ for minimal detectable binding that also parallel those required for LH release.

Affinity columns are widely used for the purification of biologic principles. An affinity column is a matrix that contains specific groups reactive with an enzyme, antibody or receptor. For instance, a column containing IgG can be used for the absorption of an antibody to IgG to the exclusion of contaminating antibodies or other serum proteins (see, Sternberger L A, Donati E J, Pouul E J, Petrali J R, Cuculis J J., Exp. Mol. Path., 4:112, 1965). Similarly, receptors for acetylcholine can be isolated from columns covalently bound with specific acetylcholine-like quarternary amino groups (see, Lindstrom J, Lennon V, Seybold M, Whittingham S., Ann. NY Acad. Sci., 274:254, 1976).

It is therefore an object of this invention to provide for the simple isolation of analogues to any of the known neuropeptide hormones and thus for the preparation of a multitude of newer hormones with new and unexpected action.

It is a further object of this invention to provide a method of recovery of previously unknown, naturally occurring biologically active peptides.

It is another object of this invention to provide for a large series of new hormone analogues capable of interaction with specific receptors.

SUMMARY OF THE INVENTION

The foregoing objects and others are accomplished in accordance with the invention, generally speaking by providing previously unknown biologically active peptide analogues by mixing a known biologically active peptide with an affinity medium and separating the unknown peptide analogue. That is, the known biologically active peptide in a solution, generally an aqueous solution, is homogenized with an affinity medium, the affinity medium separated from the supernatant liquid, generally by centrifugation and the unknown biologically active peptide analogue separated from the supernatant liquid by known techniques such as, for example liquid chromotography, electrophoresis or the like.

By "affinity medium" is meant natural tissue of the brain and other organs of the body.

The discovery of the biologically active peptide analogues was made during the course of work on neurohormone receptors utilizing luteinizing hormone releasing hormone (LHRH) in immunocytochemical staining techniques.

On immunocytochemical staining of sections through brain and pituitary with anti-LHRH, (as described in Sternberger L A, Hoffman G E., Neuroendocrinology, 25:111, 1978), localization of presumptive LHRH in the median eminence of the brain and absence of localization in the pituitary is found. Pretreatment of the sections with LHRH reveals, as expected (see, Sternberger L A, Petrali J P., Cell. Tiss. Res., 162:141, 1972, and Sternberger L A, Petrali J P, Joseph S A, Meyer H G, Mills K R., Endocrinology, 102:63, 1978), the localization of the added LHRH to gonadotroph cells of the pituitary. However, surprisingly, the staining in the brain has entirely disappeared. This observation leads to the conclusion that LHRH is never available in paraffin sections for detection by immunocytochemistry. Instead, the substance detected is a new analogue or precursor of LHRH that cross-reacts with LHRH on antibodies to LHRH. Added LHRH exchanges itself with this analog. Fixed brain acts as its own affinity medium for binding and release of the new analogue. The analogue is found to be reactive with pituitary receptors in the same manner as LHRH; therefore, it is hormonally active. Furthermore, the material is capable of reattaching itself to physiologic sites of LHRH secretion, thus further strengthening the suggestion that it represents the true LHRH carried in fibers, and raising the suspicion that the conventional decapeptide LHRH may be a breakdown product of natural LHRH.

Additionally, the process in accordance with this invention is applicable to the recovery of analogues of other biologically active peptides such as, vasopressin, oxytocin and the like. A large number of small peptides, hitherto considered the main principles of physiologic neuropeptide action, may, indeed, be breakdown products of larger, physiologic analogues and the small peptide may not necessarily be the only or even most important physiologic hormones in their respective systems.

DETAILED DESCRIPTION OF THE INVENTION

The presence of previously unknown biologically active peptide analogues by homogenation with an affinity medium (brain tissue) and subsequent separation by liquid chromatography, for example, is established by the following procedure.

Adjacent paraffin sections of Bouin-fixed rat hypothalami were treated either with buffer or with luteinizing hormone-releasing hormone (LHRH) before immunocytochemical staining with anti-LHRH. Upon buffer pretreatment, pituitary gonadotrophs were unstained and hypothalamic fibers stained. Upon LHRH pretreatment, pituitary gonadotrophs were stained (receptor reaction) and hypothalamic fibers unstained. Extension of washes and use of series of neutralizing antisera between LHRH application and immunocytochemical staining, as well as the absence of inhibiting concentrations of LHRH in the later washes and neutralizing antisera removed from the sections, excluded the possibility that the disappearance of visualization of hypothalamic fibers was due to blockage of anti-LHRH in immunocytochemical staining. The results suggested that LHRH removed from the sections an immunocytochemically stainable, as yet unknown analog of LHRH and replaced it with LHRH, which in turn became lost during subsequent immunocytochemical processing. This was confirmed by the isolation by high pressure liquid chromatography of a peak, distinct from LHRH, upon treatment of hypothalami with LHRH. It is believed that the new substance may be carrier-held and that this substance, rather than LHRH, is normally detected by immunocytochemistry with anti-LHRH. Added LHRH not only binds with high affinity pituitary receptors but also with low affinity hypothalamic carriers.

Projections, presumed to contain the decapeptide, LHRH, are revealed by immunocytochemistry with anti-LHRH over wide areas in the brain. Visualization of LHRH in vibratome and even paraffin sections of fixed tissue appears surprising as the decapeptide possesses no primary amine that is readily reactive with common aldehyde fixatives. Also, LHRH is highly soluble in water and alcohols used during fixation, embedding and immunocytochemical staining.

In work intended to reveal LHRH receptors not only in the pituitary, (as described in Sternberger L A & Petrali J P (1975), Cell Tiss. Res. 162, 141–176, and Sternberger L A, Petrali J P, Joseph S A & Mills K M (1978), Endocrinology 102, 63–73) but also in the rest of the brain, parasagittal sections of Bouin-fixed brains were treated with LHRH prior to immunocytochemical processing with anti-LHRH. Adjacent control sections were treated with buffer instead of LHRH. The control sections revealed the expected fiber staining in the median eminence, hereinafter referred to as ME, and absence of staining in the pituitary. The LHRH-treated sections revealed receptor staining in pituitary gonadotrophs but exhibited, despite washing after LHRH treatment, complete disappearance of staining in ME.

Two explanations are conceived for this unexpected disappearance of fiber staining. Perhaps, a sufficient concentration of added LHRH is held on the section, despite washing, to inhibit the anti-LHRH staining reaction. Alternatively, LHRH proper is never available in fixed, paraffin sections for staining with anti-LHRH. Instead the factor demonstrated is an LHRH analog, cross-reactive with anti-LHRH, that is held in the tissue by a carrier. Treatment with excess LHRH exchanges the analog with LHRH, which, however, because of its high solubility, is lost during subsequent immunocytochemical processing.

An attempt was made to distinguish between the two possibilities by extending the washing procedure after application of LHRH and by treating sections repeatedly with anti-LHRH prior to staining, so as to neutralize any remaining LHRH in the section. In addition, washes and neutralizing antisera were analyzed for presence of LHRH in concentrations sufficient to inhibit immunocytochemical staining. On the basis of these experiments it was concluded that, indeed, the factor stained with anti-LHRH is removed from the sections by LHRH pretreatment. The data suggested an isolation procedure for this factor and its identification by high pressure liquid chromatography (HPLC), which is set forth in the following Examples and accompanying Tables.

EXAMPLE 1

(METHOD OF ISOLATING LHRH ANALOGUE)

Dissected hypothalami (with or without pituitaries) and cerebella of eight male Sprague-Dawley rats perfused with Bouin's fixative (paraformaldehyde, picric acid, acetic acid) were brought through two changes of 50% ethanol for 1 hr each, three changes of 70% ethanol for a total of 20 hrs, two changes of 95% and 100% ethanol for 1 hr each and then returned to water by reversing the alcohol series. The tissues were then placed in siliconized glass tubes and homogenized with a de Virtis homogenizer in 0.5 ml of $10^{-4}$ M LHRH, left at 4° C. for 24 hrs and centrifuged at 1000 g at 1° C. for 60 min. The supernatants were used for high pressure liquid chromatography (HPLC).

EXAMPLES 2-7

(FURTHER CONFIRMATION OF THE ANALOGUE)

Male Sprague-Dawley rats were perfused with Bouin's fixative (paraformaldehyde, picric acid, acetic acid) and blocks of hypothalami with attached pituitary were embedded in paraffin. Seven micron-thick serial sections were used for immunocytochemistry. The immunocytochemical staining sections were pretreated with LHRH in Tris saline containing 0.25% human serum albumin (see, Sternberger L A & Petrali J P (1975) Cell Tiss. Res. 162, 141–176) or in the same solution devoid of LHRH, then washed and immunostained with anti-LHRH (see, Sternberger L A, Petrali J P, Joseph S A & Mills K M (1978) Endocrinology 102, 63–73) diluted 1:1000, sheep antirabbit immunoglobulin G diluted 1:20, peroxidase-antiperoxidase complex (PAP) diluted 1:80 to a concentration of 0.012 mg peroxidase and 0.033 mg antiperoxidase/ml (see, Sternberger L A, Hardy P H, Cuculis J J, & Meyer H G (1970) J. Histochem. Cytochem. 18, 315–333), and 0.05% diaminobenzidine tetrahydrochloride and 0.01% hydrogen peroxide with the occasional addition of $4 \times 10^{-6}$ M cobalt chloride (see, Adams J C (1977) Neuroscience 2, 141–145).

For HPLC, 50 $\mu$l of supernate was injected into a —Bondapak $C_{18}$ column and eluted with ammonium acetate (10 mM)/acetonitrile 80:20. Standardization of LHRH was carried out by injecting 50 $\mu$l of $2.5 \times 10^{-5}$ LHRH in water or in Bouin's fixative.

Results

Pretreatment of sections with LHRH resulted in appearance of gonadotroph staining and disappearance of hypothalamic staining. Concentrations of $5 \times 10^{-5}$ M LHRH brought about complete abolition of ME stainings when volumes of 0.4 ml were used, but a small amount of staining remained when the volume was 0.05 ml. Concentrations of $10^{-3}$ M resulted in complete disappearance of staining even with volumes of 0.05 ml.

Experiments to distinguish whether the abolition of ME staining was due to inhibition of anti-LHRH by LHRH carried through the washings to the staining antiserum, or alternatively, to removal of an immunoreactive LHRH analog from the ME by treatment with LHRH, were as follows:

1. Increases of number of washes after LHRH treatment from 3 to 7
2. Increases of total washing time from 15 min to 24 hrs
3. Washing under continuous magnetic stirring
4. Addition of several treatments with anti-LHRH for periods of 24 hrs in between the washing steps, to neutralize any LHRH loosely bound to the sections.
5. Assaying the washes for LHRH
6. Assaying the neutralizing anti-LHRH's for LHRH after recovery from the sections.

It was found that neither increases in number or time of washes, nor addition of stirring during washes, nor addition of antisera to neutralize any remaining LHRH, interfered with the staining abolition effect (see Table I). While the first washes may at times have contained LHRH in sufficient concentration to inhibit staining with anti-LHRH (Table II), the third washes did not. None of the washes from experiments 5A and B contained sufficient LHRH to be detected by HPLC. The 1st neutralizing antiserum contained sufficient LHRH to inhibit staining, when obtained from sections pretreated with 0.4 ml of $5 \times 10^{-5}$ LHRH. The 2nd and 3rd neutralizing antisera were only inhibitory when used at a dilution of 1:1000, but not 1:100. None of the 4th applications of antiserum contained sufficient LHRH to neutralize their staining ability. In case of pretreatment with 0.05 ml of $10^{-5}$ M LHRH, even the 1st antiserum failed to contain concentrations of LHRH that inhibited its staining ability for fibers in the ME. Thus, after three washes and several anti-LHRH treatments, sections were depleted of any LHRH that could have inhibited the final anti-LHRH used for immunocytochemical staining. Furthermore, sections were washed another three times after the final neutralizing antiserum and exposed to 3% normal sheep serum for 30 min prior to immunostaining with anti-LHRH. These results made it unlikely that the ME staining abolition effect was due to inhibition of the final immunostaining anti-LHRH by any LHRH carried through the washing procedure. Lastly, the minimal concentration of LHRH for pituitary receptor staining was found to be $10^{-7}$ M when 0.05 ml applications were followed by extensive washes (experiment 7, Table I), but $10^{-10}$ M when admixed with the staining antiserum. The difference in concentration required for receptor staining shows that the washes were effective in removing most of the LHRH even when bound by high affinity receptors (see, Sternberger L A, Petrali J P, Joseph S A & Mills K M (1978) Endocrinology 102, 63–73). It would appear, therefore, that the washes certainly would be effective in removing any loosely bound LHRH prior to application of the immunostaining anti-LHRH.

These experiments establish that the ME staining abolition effect was not due to inhibition of anti-LHRH used in immunostaining, but rather to specific removal from the ME of a substance immunostained by anti-LHRH. This is confirmed when LHRH was used as a specific solvent for extraction of this hypothetical substance from hypothalamus. In each of four Bouin-fixed hypothalami, this procedure eluted a specific peak corresponding to a substance less hydrophobic than LHRH itself. No such substance was eluted from four other hypothalami extracted with water instead of LHRH. However, when the water extraction was followed by LHRH, the new peak had reappeared. The peak was undetectable when LHRH extracts of cerebella were chromatographed.

The above experiments show that LHRH removes a specific substance from Bouin-fixed hypothalamus. In the absence of LHRH treatment, this substance is stainable with anti-LHRH by immunocytochemistry. Therefore, staining normally ascribed to LHRH is not due to the decapeptide itself, but rather to another substance immunologically cross-reactive with it. This substance appears to be less hydrophobic than LHRH. Since LHRH itself is poor in hydrophilic amino acids, it is likely that this new substance possesses amino acids additional to those found in the decapeptide. However, the substance is not a macromolecule unable to pass through the column used.

The present experiments suggest that all LHRH is lost and that the only substance detectable by immunocytochemistry is an analog more tightly bound to the tissue. Bonding is done to a carrier through amino acids common to those found in LHRH. This permits bonding to the carrier not only by the new substance, but also by LHRH. The new substance can be exchanged for LHRH, provided the concentration is high, suggesting that LHRH is bound with lower affinity than the new substance. Once the new substance is displaced by low affinity-bound LHRH, the LHRH itself is easily lost during washings. The higher affinity for the carrier by the new substance is mediated through its additional amino acids, possibly via dimerization effected by them (see, Sternberger L A. (1979) Immunocytochemistry, 2nd Edition (John Wiley and Sons, New York).

Fixation in Bouin's fixative did not apparently destroy the ability of the hypothetical carrier to exchange the new substance for LHRH. This is reminiscent of the unique ability of picric acid-paraformaldehyde fixatives to preserve the binding activity of peptide hormone receptors (see, Sternberger, L. A. & Petrali, J. P. (1975) Cell Tiss. Res. 162, 141–176; Sternberger, L. A., Petrali, J. P., Joseph, S. A. & Mill, K. M. (1978) Endocrinology 102, 63–73; and Salih, H., Murthy, G. S. and Friesen, H. G. (1979) Endocrinology 105, 21–26. Furthermore, even in the amine reagent-treated immunoglobulin molecule, the hypervariable regions seemed to be more resistant to destruction of their ability for reaction with antigen than epitopes in other molecular regions for reaction with second antibody (see, Sternberger, L. A. & Petrali, J. P. (1977) J. Histochem. Cytochem. 25, 1036–1042 and Tougard, C., Tixier-Vidal, A. & Avrameas, S. (1979) J. Histochem. Cytochem. 27, 1630–1633. The use of fixed tissue for elution of the new substance from hypothalamus presumably prevented solubilization of extraneous constituents that could have masked the peak specifically eluted by LHRH. Thus, fixed brain apparently acted as its own affinity medium for purification of the new substance.

TABLE I

Effect of extended washes and of neutralizing antisers on the abolition of immunostaining with anti-LHRH by pretreatment with LHRH

| | Procedure | | | | | | | Extender Washes |
|---|---|---|---|---|---|---|---|---|
| | Standard | | | Neutralization + Extended Washes | | | | |
| Experiment No. | 2 | 3 | 4A | 4B | 5A | 5B | 6 | 7 |
| | (3% normal sheep serum for 30 min-all experiments) | | | | | | | |
| LHRH[a] ml | 0.4 | 0.4 | 0.4 | 0.4 | 0.05 | 0.05 | 0.05[c] | 0.075 |
| molarity[b] | $5 \times 10^{-5}$ | $5 \times 10^{-5}$ | $5 \times 10^{-5}$ | $5 \times 10^{-5}$ | $5 \times 10^{-5}$ | $5 \times 10^{-5}$ | $10^{-3}$ | $10^{-3}$ |
| time | 1 hr | 1 hr | 1 hr | 1 hr | 1 hr | 1 hr | 24 hr | 24 hr |
| Preliminary rinse[d] | no | no | no | no | no | no | yes | yes |
| Washes[e] | S | S | S | S | S | A | A | A |
| No. of washes | 3 | 3 | 3 | 3 | 3 | 3 | 3 | 7 |
| ml each | 140 | 140 | 140 | 140 | 140 | 200 | 200 | 200 |
| time each | 5 min[f] | 5 min | 5 min | 5 min | 10 min[f] | 10 min[f] | 10 min | 6 × 1hr +1 × 18 |
| 3% normal sheep serum 10 min, ml | — | 0.4 | 0.4 | 0.4 | 0.05 | 0.05 | 0.05 | — |
| Neutralizing antiserum[g] dilution | — | $10^{-3}$ | $10^{-2}$ | $10^{-3}$ | $10^{-3}$ | $10^{-3}$ | $10^{-3}$ | — |
| No. of applications | | 1 | 4 | 4 | 4 | 4 | 1 | |
| ml each | | 0.4 | 0.4 | 0.4 | 0.05 | 0.05 | 0.05 | |
| time | | 2.5 hr[f] | 3 × 1 hr + 1 × 18 hr[f] | 3 × 1 hr + 1 × 18 hr[f] | 3 × 1 hr + 1 × 18 hr[f] | 3 × 1 hr + 1 × 18 hr[f] | 24 hr | |
| Repeat washes | | S | S | S | S | A | A | |
| number of washes | — | 3 | 3 | 3 | 3 | 3 | 3 | — |

TABLE I-continued

| | | | | | | |
|---|---|---|---|---|---|---|
| ml each | 140 | 140 | 140 | 140 | 200 | 200 |
| time each | 5 min | 5 min | 5 min | 10 min[f] | 10 min[f] | 10 min |

Followed in each case by 3% normal sheep serum for 30 min, anti-LHRH for 24 hr, PAP for 30 min and diaminobenzidine and hydrogen peroxide for 8 min.

Staining Results

| Experiment No. | 2 | 3 | 4A | 4B | 5A | 5B | 6 | 7 |
|---|---|---|---|---|---|---|---|---|
| Pituitary gonadotrophs | | | | | | | | |
| −LHRH[h] | − | − | − | − | − | − | − | − |
| +LHRH | + | + | + | + | + | + | + | + |
| Median eminence | | | | | | | | |
| −LHRH | + | + | + | + | + | + | + | + |
| +LHRH | − | − | − | − | = | = | − | − |

[a] LHRH was substituted by buffer in controls.
[b] In most experiments a wide range of concentrations was used for affinity determination, but for the purpose of the present table only the highest concentration is listed.
[c] 0.05 ml LHRH placed on section, shaken off imediatley and replaced for 24 hr to avoid dilution.
[d] Slides were rinsed with 10 ml of 0.05 M Tris saline (4) prior to immersion into wash solution.
[e] 0.05 M Tris saline. S, static wash. A, washing under continuous agitation.
[f] Washes and antisera transferred onto fresh slides to establish presence of eluted LHRH (see Table II). In addition, washes from experiment 4 were assayed by HPLC.
[g] Anti-LHRH was applied to neutralize any LHRH remaining on the section.
[h] Controls in which LHRH was substituted by buffer.

TABLE II

Staining of ME as assay for LHRH in washes and antisera recovered from LHRH-treated section.

| Experiment No. | 1st | 2nd | 3rd | 4th |
|---|---|---|---|---|
| | | Wash No. | | |
| 2 | | | + | |
| 5A | − | | | |
| 5B | + | | | |
| | | Neutralizing Antiserum | | |
| 3 | − | | | |
| 4A | − | + | + | + |
| 4B | − | − | − | + |
| 5A | + | | | + |
| 5B | + | | | + |

Antisera used to neutralize any LHRH remaining on the sections from Table I were reapplied to fresh sections as primary antisera in the PAP procedure to estimate inhibition of staining of fibers in ME. Washes from Table I were similarly reapplied after admixture with equal volumes of anti-LHRH (final dilution 1:1000).

What is claimed is:

1. A process for obtaining a neuropeptide analogue from brain or other organ of the body comprising adding a neuropeptide to brain or other organ of the body, the neuropeptide being present in an amount sufficient to displace the neuropeptide analogue from brain or other organ of the body, and isolating the neuropeptide analogue.

2. The process of claim 1 wherein the neuropeptide in solution is homogenized with the natural tissue of brain and other organs of the body, the supernatant is separated from the natural tissue of brain and other organs of the body and the neuropeptide analogue isolated from the supernatant.

3. The process of claim 1 wherein the neuropeptide is luteinizing hormone—releasing hormone.

4. The process of claim 1 wherein the neuropeptide is vasopressin.

5. The process of claim 1 wherein the neuropeptide is oxytocin.

* * * * *